United States Patent [19]
Rajan et al.

[11] Patent Number: 5,891,131
[45] Date of Patent: Apr. 6, 1999

[54] METHOD AND APPARATUS FOR AUTOMATED SIMULATION AND DESIGN OF CORNEAL REFRACTIVE PROCEDURES

[75] Inventors: Subramaniam D. Rajan, Chandler; Barzin Mobasher, Scottsdale; Gary W. Hall, Paradise Valley, all of Ariz.

[73] Assignee: Arizona Board of Regents, Tempe, Ariz.

[21] Appl. No.: 12,051

[22] Filed: Feb. 1, 1993

[51] Int. Cl.$^6$ .......................... A61B 17/36; G06F 159/00; A61F 9/013

[52] U.S. Cl. .................................. 606/5; 606/6; 351/212

[58] Field of Search .................. 364/413.25, 413.01, 364/413.13; 606/3, 5, 4, 6, 10, 12, 14, 166; 351/212; 128/653.1, 660.07

[56] References Cited

U.S. PATENT DOCUMENTS 4,669,466   6/1987   L'Esperance ........................ 128/303.1

OTHER PUBLICATIONS

"On the Computer–Aided and Optimal Design of Keratorefractive Surgery" Velinsky, et al., *Refractive and Corneal Surgery*, vol. 8, p. 173, Mar./Apr. 1992.

"Intraocular Lens Design with MSC/pal", Frazone, et al., 1985 MSC/NASTRAN User's Conference in Pasadena, CA.

"Corneal Curvature Change Due to Structual Alternation by Radial Keratotomy", Bisarnsin, et al. *ASME Journal of Biomedical Engineering*, vol. 110, pp. 249–253, 1988.

"Reduction of Corneal Astigmatism at Cataract Surgery", Hall, et al. *Journal of Cataract Refractive Surgery*, vol. 17 pp. 407–414, Jul. 1991.

"Numerical Modeling of Radial Astigmatic, and Hexagonal Keratotomy" by Peter M. Pinsky, Ph.D and Deepak V. Datye. Mtech, *Refractive & Corneal Surgery*, vol. 8, pp. 164–172 (Mar./Apr. 1992).

*Primary Examiner*—Joseph Thomas
*Attorney, Agent, or Firm*—David G. Rosenbaum

[57] ABSTRACT

A technique for automated design of a corneal surgical procedure includes topographical measurements of a patient's eye to obtain corneal surface topography. Conventional techniques are used to obtain the thickness of the cornea and the intraocular pressure. The topographical information is interpolated and extrapolated to fit the nodes of a finite element analysis model of the eye, which is then analyzed to predict the initial state of stress of the eye and obtain pre-operative curvatures of the cornea. Incision data constituting the "initial" surgical plan is incorporated into the finite element analysis model. A new analysis then is performed to simulate resulting deformations, stresses, and curvatures of the eye. They are compared to the original values thereof and to the vision objective. If necessary, the surgical plan is modified, and the resulting new incision data is entered into the model and the analysis is repeated. This procedure is repeated until the vision objectives are met.

29 Claims, 7 Drawing Sheets

METHOD AND APPARATUS FOR AUTOMATED SIMULATION AND DESIGN OF CORNEAL REFRACTIVE PROCEDURES

BACKGROUND OF THE INVENTION

The invention relates to systems and techniques for mathematically modeling a human eye using topographical data measured from a human eye, using the mathematical model to simulate deformation of the eye by hypothetical incisions or excisions or ablations to arrive at an optimum surgical design by identifying the number, shape, location, length, and depth of the incisions or excisions or the shape, location, and quantity of corneal ablation(s). (It should be understood that hereinafter, including in the claims, the term "incision," which usually refers to a cut made by a scalpel, and the term "excision," which usually refers to a cut made by a laser beam, are considered to be interchangeable and to have the same meaning.)

Modern corneal refractive surgery originated with the work of Dr. Svyatoslav Fyodorov of Moscow and Dr. Jose Barraquer of Bogota, Columbia. Subsequently, various surgical techniques have been developed to alter the curvature of the cornea to correct refractive errors. The various techniques include incisional keratotomy using diamond blades, excisional keratotomy using laser beams to photo-disrupt molecules and ablate tissue in a linear pattern, ablative keratectomy or photo-refractive keratectomy using laser beams to remove larger areas of corneal tissue, mechanical removal and reshaping of corneal tissue (keratomileusis), and implantation of human or synthetic materials into the corneal stroma. All of the known procedures alter central corneal curvature by changing the structure of the cornea. All such refractive procedures are characterized by difficulty in predicting both the immediate and long term results, because of errors in calculations of pre-surgical measurements, failure to precisely implement the planned surgical techniques, and biological variances which affect immediate and long term results.

The cornea traditionally has been treated as a spherocylindrical lens, assuming that the radius of each individual meridian from the corneal apex to the corneal periphery is uniform. Prior methodologies tend to use an approximation to the topographic information of the cornea to determine the refractive power of the eye. In one known procedure, circular mires (reflected light images from the cornea conventionally used to mathematically calculate corneal curvature) are reflected from the corneal surface, and the difference between a given point on the mire and an adjacent mire is measured. A semi-quantitative estimate of the surface curvature is obtained by comparing this measurement with the values obtained using spheres of various radii. Prior mathematical models use a variety of approximations such as a simplified form of the corneal surface (e.g., spherical) or assume a symmetrical cornea (leading to a quarter model or an axisymmetric model) or use simplified material properties (e.g., isotropic), or assume small deformations or displacements, or do not consider clinically obtained data in the construction of the mathematical model.

Perhaps the closest prior art is indicated in the article "On the Computer-Aided and Optimal Design of Keratorefractive Surgery," by Steven A. Velinsky and Michael R. Bryant, published in Volume 8, page 173 of "Refractive and Corneal Surgery," March/April 1992. This article describes a computer-aided surgical design methodology, proposing that it could be an effective surgical design aid for the refractive surgeon, wherein the surgeon could choose constraints on surgical parameters such as minimum optical zone size, maximum depth of cut, etc., measure the patient's corneal topography, refractive error and possible other ocular parameters, and then review the computed results. The article refers to several mathematical models described in the literature, and how such mathematical models might be helpful. However, the article fails to disclose any particular adequate mathematical model of the cornea or any specific recommendation of surgical design that has been validated with clinical data.

The prior radial keratotomy procedures frequently result in large amounts of undercorrection or overcorrection. Prior keratotomy procedures often are based on experiential use of nomograms indicating appropriate surgical designs for a particular patient based on age, sex, refractive error, and intraocular pressure.

Finite element analysis is a known mathematically-based numerical tool that has been used to solve a variety of problems that are described by partial differential or integral equations. This technique has been used primarily in the area of solid mechanics, fluid mechanics, heat transfer, electromagnetics, acoustics, and biomechanics, including designing remedial techniques being developed for the human eye, to model internal structure and stresses in relation to various configurations of intraocular devices and corneal implants, as described in "Intraocular Lens Design With MSC/pal," by A. D. Franzone and V. M. Ghazarian in 1985 at the MSC/NASTRAN User's Conference in Pasadena, Calif., and in "Corneal Curvature Change Due to Structural Alternation by Radial Keratotomy," by Huang Bisarnsin, Schachar, and Black in Volume 110, pages 249–253, 1988 in the ASME Journal of Biomedical Engineering. Also see "Reduction of Corneal Astigmatism at Cataract Surgery," by Hall, Campion, Sorenson, and Monthofer, Volume 17, pages 407–414, July 1991 in the Journal of Cataract Refractive Surgery.

There clearly is an unmet need for an improved system for accurately predicting outcomes of hypothetical surgical procedures on the cornea to aid in the design of minimally invasive corneal surgery. There is an unmet need for a totally automated way of determining an optimal design of a surgical plan for incisional or excisional keratotomy or ablative keratectomy surgery to meet predetermined visual objectives with minimum invasiveness and minimum optical distortion. Further, it would be desirable to provide a technique for designing a multi-focal cornea that is similar to a gradient bifocal for patients that have presbyopia. It would be desirable to have an accurate mathematical model of the cornea for use in developing new surgical procedures without experimenting on live corneas.

SUMMARY OF THE INVENTION

Accordingly, it is an object of the invention to provide a minimally invasive surgical procedure for corneal surgery for a human eye to achieve predetermined modified characteristics of that eye.

It is another object of the invention to provide a system and method which result in improved predictability of outcomes of corneal surgery.

It is another object of the invention to provide an improved method and apparatus for design of optical surgery that minimize invasiveness of the surgical procedure.

It is another object of the invention to provide a method and apparatus for surgical design which result in reduction or elimination of postoperative irregular astigmatism.

It is another object of the invention to provide an improved apparatus and method for surgical design which result in reduced multifocal imaging of the central cornea, thereby enhancing contrast sensitivity and improving vision under low light illumination conditions.

It is another object of the invention to provide an improved finite element analysis model of the human eye, including back-calculation of values of material properties of the cornea and sclera, which incorporate the measured topography of that eye and more accurately predict deformations of the cornea due to a hypothetical group of modeled incisions and/or excisions and/or ablation than has been achieved in the prior art.

It is another object of the invention to provide a system and method for providing an optimal surgical design for a human eye to achieve desired optical characteristics thereof.

It is another object of the invention to reduce the likelihood of postoperative complications in the eye including, but not limited to overcorrection or undercorrection of pre-existing refractive errors.

It is another object of the invention to provide a "training tool" or "surgery simulator" for surgeons who need to gain experience with corneal refractive surgery.

It is another object of the invention to provide a means for designing new surgical procedures without the need for experimentation on live human beings.

Briefly described, and in accordance with one embodiment thereof, the invention provides a system for simulating deformation of a cornea as a result of corneal incisions, excisions and ablations in order to effectuate automated "surgical design" of a patient's eye in response to topographic, ultrasonic, and other measurements of the patient's eye. A finite element analysis model of the eye is constructed. Measured x,y,z coordinate data are interpolated and extrapolated to generate "nearest-fix" x,y,z, coordinates for the nodes of the finite element analysis mode. Measured thicknesses of the eye are assigned to each element of the finite element model. Pre-operative values of curvature of the cornea are computed. In one embodiment of the invention, Young's modulus is "back-computed" from measured values of corneal deformations at different pressure loads. An initial estimated surgical plan, including a number of incisions, locations of incisions, incision orientations, incision depth and incision lengths is introduced into the shell finite element analysis model by introducing duplicate "nodes" and nonlinear springs along the initial hypothetical incisions. Or, ablations may be included in the estimated surgical plan introduced into the finite element analysis model by varying the thickness and/or material property constants of the elements in the ablated region. A geometrically and materially nonlinear finite element analysis then is performed by solving the equations representing the finite element analysis model in response to incremental increases in intraocular pressure until the final "equilibrium state" is reached. Postoperative curvatures of the cornea are computed and compared to pre-operative values and to vision objectives. If the vision objectives are not met, the surgical model is modified and the analysis is repeated. This procedure is continued until the vision objectives are met. In one embodiment, a boundary element analysis model is used instead of a finite element analysis model.

DETAILED DESCRIPTION OF THE PREFERRED EMBODIMENTS

The present invention involves constructing a model of a human eye using a suitable three-dimensional finite element analysis (FEA) model which includes a mesh that generally corresponds to the shape of the human eye. The shape of the human eye is described by the finite element mesh obtained using data measured from a corneal mapping device and translated into the nodal points of the FEA model. The nodal points in a small region are connected to each other, to form a finite set of elements. The elements are connected to each other by means of sharing common nodes. The thickness values at any particular region are obtained using ultrasonic measuring devices, and are applied to the elements. The "loading" of the finite element mesh structure is represented by the intraocular pressure, and the resistance of the structure to such applied "loading" is measured by the stiffness of the structure, which is computed on the basis of its geometry, boundary conditions, and its material properties, namely Poisson's ratio v, and Young's modulus E.

In the area of structural mechanics, finite element analysis formulations are usually based on the "principle of virtual work," which is equivalent to invoking the stationary conditions of the total potential energy, $\Pi$, given by $$\Pi = \frac{1}{2} \int_V \underline{\epsilon}^T \underline{D} \underline{\epsilon} \, dV - \int_V \underline{Z}^T \underline{f}^B dV - \int_S \underline{Z}^{S^T} \underline{f}^S dS \tag{1}$$

where $$\underline{\epsilon} = \underline{B} \underline{Z} \tag{2}$$

and $$\underline{\sigma} = \underline{D} \underline{\epsilon} \tag{3}$$

$\epsilon^T$ is the transpose of the strain vector, $\underline{Z}^T$ is the transpose of nodal displacement vector, and $\underline{Z}^{S^T}$ is the transpose of the nodal displacement vectors on the surface. $\underline{Z}$ and $\underline{Z}^S$ are nodal displacement terms associated with nodal loads. In the above equations, the various symbols have the following meanings:

ε represents the strain vector $\underline{D}$ represents the material matrix $\underline{Z}$ represents the vector of nodal displacements $\underline{f}^B$ represents the nodal body force vector $\underline{f}^S$ represents the nodal surface traction vector dV represents differential volume dS represents differential surface area σ represents the stress vector $\underline{B}$ represents a strain-displacement matrix V represents volume S represents surface area.

The first term on the right hand side of the equation (1) is the strain energy of the structure, and the second and third terms represent the total work accomplished by the external forces and body forces. The strain energy is a function of the strains and stresses that are related to each other via the material matrix D. The material properties that contribute to the material matrix D include the modulus of elasticity (Young's modulus) and Poisson's ratio. In a uniaxial state of stress, Poisson's ratio is defined as:

$$\epsilon_{lat.} = -\nu \epsilon_{long.}, \quad (4)$$

where $\epsilon_{lat}$ is the normal strain in the lateral direction and $\epsilon_{long}$ is the normal strain in the longitudinal direction. In a uniaxial state of stress, Young's modulus E is defined according to $$\sigma_{zz} = E\epsilon_{zz}, \quad (5)$$

where $\sigma_{zz}$ is the normal stress and $\epsilon_{zz}$ is the normal strain. The work accomplished is a function of the applied loads and surface tractions.

Using an assumed displacement field, the minimization of the total potential energy Π leads to the element equilibrium equations of the form $$\underline{k}_{n \times n} \times \underline{z}_{n \times 1} = \underline{r}_{n \times 1}, \quad (6)$$

where the expression $$\underline{k}_{n \times n} = \int_V \underline{B}^T \underline{D} \underline{B} dV$$

is the element stiffness matrix, and $z_{n \times 1}$ is the vector of element nodal displacements $\underline{r}_{n \times 1}$ is the vector of element nodal forces. Since the entire structure is assumed to be in equilibrium, the assembly of the element equations leads to the structural equilibrium equations of the form $$\underline{K}_{N \times N} \times \underline{Z}_{N \times 1} = \underline{R}_{N \times 1} \quad (7)$$

where $\underline{K}_{N \times N}$ is the structural stiffness matrix, $\underline{Z}_{N \times 1}$ is the vector of nodal displacements and $\underline{R}_{N \times 1}$ is the vector of nodal forces. These algebraic equations are finally solved for $\underline{Z}$ in a variety of ways depending on whether the structural behavior is linear or nonlinear.

A commercially available finite element analysis program which effectively solves these equations after the appropriate values and boundary conditions have been assigned to the various nodes and the appropriate material properties have been assigned to the various elements defined by the connectivity of the nodes is called ABAQUS, available from HKS, Inc. of Providence, R.I. Creating the FEA model for purposes of the present invention simply involves inputting to the ABAQUS program the x,y,z coordinates for each node, inputting the forces that act on the nodes and/or elements, assigning the boundary conditions to each node, defining the nodal connectivity that defines each element, and inputting the eye material properties and thickness or stiffness to each defined element along with other input data, such as whether the analysis is linear or non-linear, or the properties and definitions of the non-linear springs.

It should be noted that there are two popular approaches to solving finite element analysis problems, one being the above-described approach of minimizing total potential energy (or, variational approach), the other being a method of weighted residuals which operates on partial differential equations defining the problem. The first approach is generally recognized to be simpler, and is implemented by the above ABAQUS program, but the invention could be implemented by the second approach.

Figure 1:
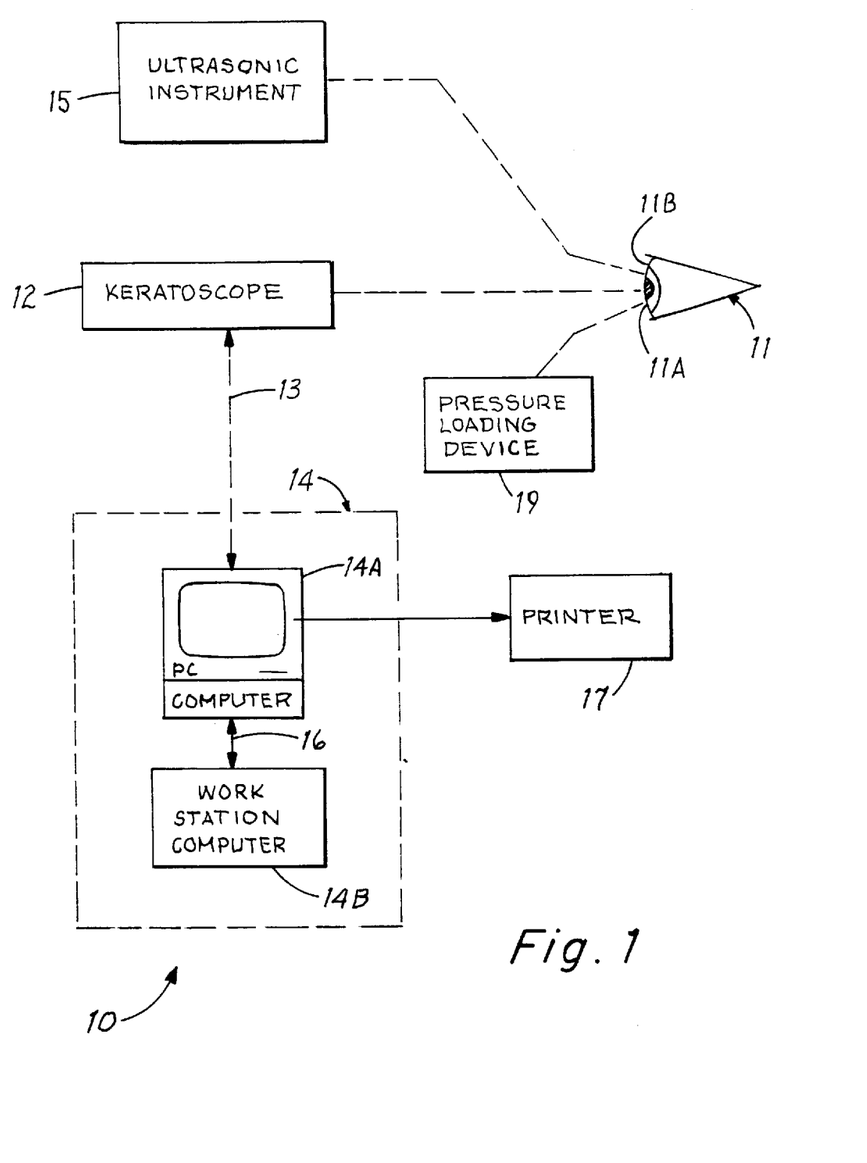
FIG. 1 is a block diagram illustrating the components used in the invention.

FIG. 1 shows an apparatus used in conjunction with the present invention. An ultrasonic instrument 15, such as a DGH packymetor, model DGH-2000 available from DGH Technology, Inc. of Frazier, Pa., is used to obtain the thickness and intraocular pressure of cornea 11A.

A corneal topographer 12, which can be a model TMS-1, manufactured by Computed Anatomy, 28 West 36th Street, New York, N.Y., is utilized to measure the surface topography of cornea 11A. The resulting information is transferred by means of a floppy disk to a computer system 14. Alternatively, a digital data bus 13 could be provided to transfer topography information from corneal topographer 12 to computer system 14. In a prototype of the invention, system 14 includes an ordinary IBM PC type of computer 14A coupled by a RS232 cable 16 to a workstation computer 14B, which can be a Sun SPARCStation 2, marketed by Sun Microsystems, of Mountain View, Calif. A printer 17 is connected by a cable to the printer port of computer 14A.

Thickness and intraocular pressure measurements made by ultrasonic instrument 15 are obtained. This data then is used in the generation of the finite element model. However, it is possible to have this data transferred digitally, either by means of a floppy disk or a communication link, to the personal computer 14A.

A conventional pressure loading device 19 is utilized to apply a precisely measurable force on a point of the sclera as far away as practical from the cornea, so that resulting changes on the elastic cornea as a result of the new loading can be measured. Then, in accordance with the present invention, the value of Young's modulus can be "back-calculated" in the manner subsequently described. Alternately, uniform pressure loading could be achieved by applying a sealed pressure chamber to the eye and increasing the gas pressure therein. Such uniform loading may have the advantage of providing less "noise" error in the measurements. A suitable pressure loading device 19 could be an opthalmo dynamometer, commercially available from Bailliart, of Germany.

To obtain an FEA model of the patient's eye, the measured topographical data is interpolated and extrapolated using the subsequently described cubic spline technique to provide a pre-established reduced number of nodal points of a finite element mesh, with nodal coordinates which are a "close fit" to the measured corneal surface. Values of the thickness of the cornea and sclera obtained from the data obtained from ultrasonic instrument 5 are assigned to the various finite elements of the FEA model. The FEA mesh then defines a continuous surface that accurately represents the pre-operative surface of the cornea, including any astigmatism that may be present.

Figure 5:
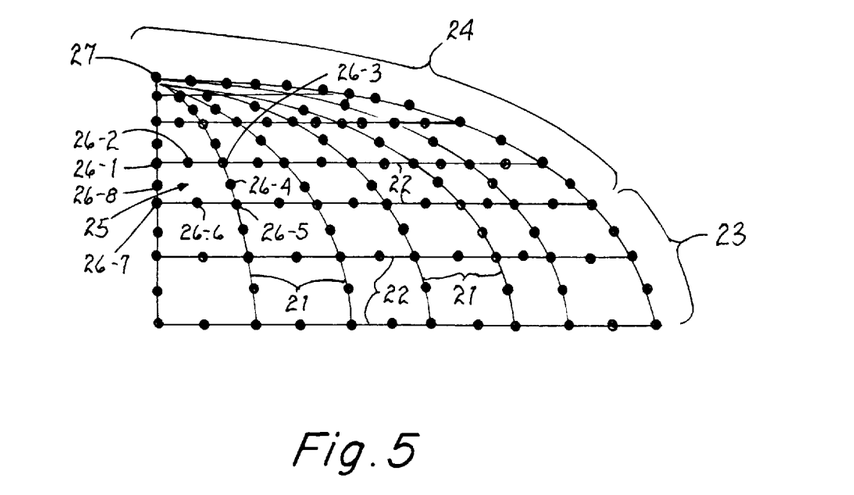
FIG. 5 is a three-dimensional diagram of the finite element mesh used in accordance with the present invention.

The curvatures of the surface then are computed at each node of the finite element analysis model. Surfaces of revolution are generated by revolving a plane curve, called the meridian, about an axis not necessarily intersecting the meridian. The meridian (defined by a radial line such as 21 in FIG. 5) is one of the principal sections and its curvature at any point is one of the principal curvatures $k_1$. (The principal curvatures are defined as the maximum and the minimum curvatures at a point on a surface.) The other orthogonal principal section is obtained by the intersection of the surface with a plane that is at right angles to the plane of the meridian and that also contains the normal. The second principal section has curvature $k_2$. If the equation of the meridian is written as $r=f(z)$, then $$k_1 = \frac{-r''}{[1+(r')^2]^{\frac{3}{2}}} \quad (8)$$

and $$k_2 = \frac{1}{r[1+(r')^2]^{\frac{3}{2}}} \quad (9)$$

$r'$ and $r''$ being the first and second derivatives of $r$, respectively.

Figure 2:
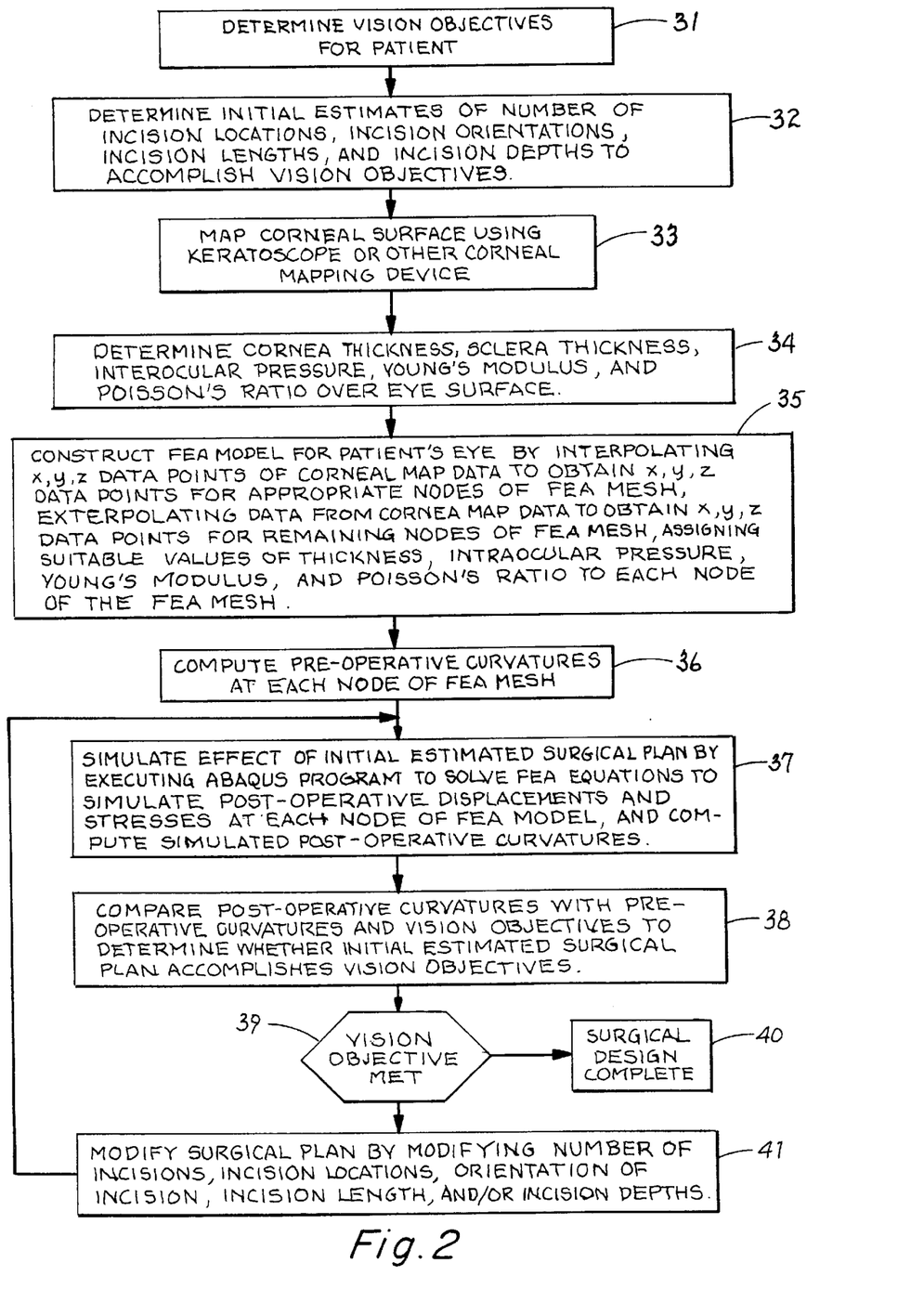
FIG. 2 is a basic flow chart useful in describing the method of the invention.

FIG. 2 is a flowchart useful in explaining the basic steps involved in use of the system shown in FIG. 1 to produce an optimum design for guiding surgery of a patient's eye. In block 31 of FIG. 2, the physician determines the "vision objectives" for the eye. The vision objectives can be specified as desired curvatures at particular locations of the cornea when the eye is in an accommodatively relaxed condition after completion of the surgery. These desired curvatures of refractive change may be determined at nodal points on the cornea by use of a spatially resolved refractometer. The vision objectives are selected to maximize the number of light rays that the eye focuses on the fovea for a given functional distance.

In block 32, the physician provides initial estimates of the number of incisions required, their locations, the orientations of various incisions, the incision lengths, and the incision depths needed in order to accomplish the vision objectives of block 31. As indicated in block 33, corneal topographer 12 is used to obtain a topographic map of a portion of the eye. The TMS-1 corneal topographer mentioned above is capable of providing an x,y,z coordinate "map" that covers most of the cornea, producing a data file from which the x,y,z coordinates of approximately 7000 points can be obtained.

As indicated in block 34 of FIG. 2, the ultrasonic instrument 15 is used to provide measurements of the thickness of the cornea and the intraocular pressure. In the prototype system presently being implemented, typical values of Poisson's ratio and Young's modulus are used. Presently, Poisson's ratio values of 0.49 are used for both the cornea and sclera. Presently, values of Young's modulus equal to $2 \times 10^5$ dynes per square millimeter are used for the cornea and $5 \times 10^5$ dynes per square millimeter for the sclera.

Preferably, Young's modulus is "back-calculated" on the basis of corneal topographical changes measured by using the corneal topographer 12 after varying a known force applied by pressure loading device 19 (FIG. 1) to the eye.

The main objective of the back-calculation procedure is to determine as accurately as possible the modulus of elasticity for the cornea and the sclera, because it also is recognized that these values vary from patient to patient, and because it also is recognized that the modulus of elasticity is one of the most crucial parameters that influences the finite element analysis predictions. To describe the basic technique of the back-calculation procedure, refer to FIG. 9, which shows three assumed states, namely State 0 in which the cornea is relaxed, State 1 in which pressure loading device 19 applies point load P1 to the sclera of eye 11, and State 2 in which pressure loading device 19 applies point load P2 to the sclera. P0 is the intraocular pressure which is uniformly applied to the inner surface of the cornea and sclera. The values of the moduli of elasticity for the cornea and the sclera, respectively, are adjusted such that the z coordinates at selected nodes are close to the values actually measured for State 1 and State 2 by TMS-1 corneal topographer 12 with the two values of point loads P1 and P2 actually applied, respectively.

Figure 9:
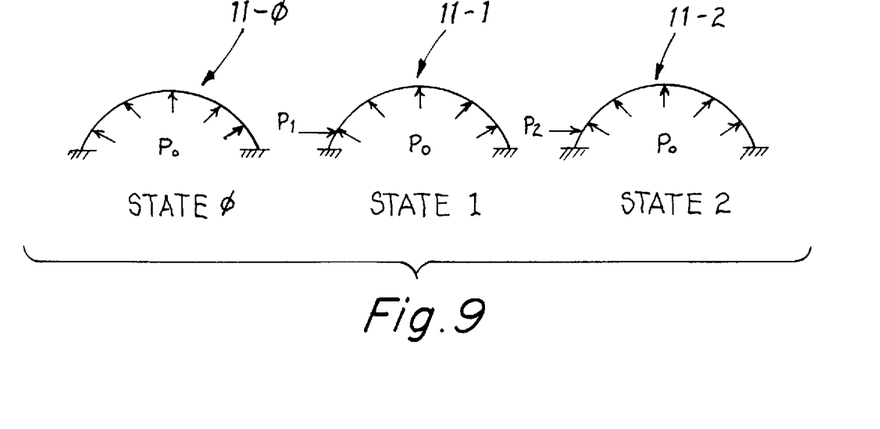
FIG. 9 is a diagram useful in explaining automated back-calculation of the modulus of elasticity of the eye.

Let $\hat{Z}_i^j$ be the observed z coordinate at a particular node i for a state j obtained using the above mentioned TMS-1 system. Let $Z_i^j$ be the computed z coordinate at a particular node i for the state j using the finite element analysis according to the present invention. The back-calculation problem then is to find the value of $\{E_c, E_s\}$ to minimize the value of the expression $$f(E_c,E_s) = \sum_{i=1}^{n} \sum_{j=1}^{2} \left( \frac{Z_i^j}{\hat{Z}_i^j} - 1 \right)^2 \quad (10)$$

with the conditions $$E_C^L \leq E_c \leq E_C^U$$

and $$E_S^L \leq E_s \leq E_S^U$$

and where $\{E_c, E_s\}$ is the vector of design variables, $f(E_c, E_s)$ is the objective function, $E_c$ is the modulus of elasticity of the cornea, $E_s$ is the modulus of elasticity of the sclera, n is the number of points at which z displacements are to be computed, and the two inequality constraints represent the lower (L) and upper (U) bounds on the two design parameters. It should be appreciated that such a problem formulation falls under the category of a non-linear programming (NLP) problem, and can be solved using various non-linear programming techniques such as the "method of feasible directions", or using a constrained least-squares technique. A commercially available program for solving such non-linear programming problems is the DOT (Design Optimization Tools) program, available from VMA, Inc. of Santa Barbara, Calif.

As indicated in block 35, an FEA model is "constructed" for the patient's eye by interpolating between the various 7000 x,y,z coordinates of the corneal map produced by TMS-1 corneal topographer 12 to provide a smaller number of representative "smoothed" x,y,z values to be assigned to the various nodes of the FEA mesh shown in FIG. 5.

FIG. 5 shows one quadrant of the FEA mesh, the other three quadrants being substantially identical except for the nodal values assigned to the nodes thereof. The FEA mesh shown in FIG. 5 includes a plurality of equi-angularly spaced radial lines 21, each extending from a cornea center or apex 27 of cornea section 24 to the bottom of sclera section 23. In the FEA mesh actually used in a prototype of the invention under development, there are 32 such radial lines 21 and also 30 generally equally spaced circumferential lines 22. Each area such as 25 that is bounded by two adjacent radial lines and two adjacent circumferential lines 22 is an "element" of the FEA model. Each typical element 25 includes eight assigned "nodes", such as nodes 26-1 ... 26-8. The four corners of a typical element such as 25 share corner nodes 26-1,3,5,7 with adjacent elements, and also share "midpoint" nodes 26-2,4,6, and 8 with corresponding midpoint nodes of adjacent elements. The nodes and the connectivity thereof which define the elements of the FEA mesh thus are illustrated in FIG. 5.

The values assigned to each node include its interpolated/extrapolated x,y,z coordinates and its boundary conditions, which are whether the node can or cannot undergo x,y,z displacements and rotations. The values assigned to each element in the FEA model include the thickness of the element, Young's modulus or modulus of elasticity, the shear modulus, and Poisson's ratio in the orthotropic directions, namely the xy, xz, and zx directions. Any external "loading" forces at each node also are assigned to that node. The orthotropic values of Poisson's ratio presently uses are $\upsilon_{xy}=0.0025$, $\upsilon_{xz}=0.0025$, and $\upsilon_{zx}=0.49$. The value of shear modulus used is $G_{yz}=6.71 \times 10^3$ dynes per square millimeter.

The objective of the tasks in block 35 is three-fold. First, the total number of nodes, and thus the elements generated from them, should be a variable, so that the mesh sensitivity of the results can be studied while the operator is given the chance to use a coarse mesh for preliminary studies. Second, the nodal points generated should be compatible with the choice of element required. For example, eight-node shell elements are used in the present approach. However, the proposed system is able to generate any type of element required, such as a 27-node hexahedral three-dimensional element, a 6-node triangular shell element, or a 9-node shell element. Third, the nodes generated must be able to provide sufficient mesh refinement or density to achieve the needed resolution. A refined mesh in the regions of primary interest such as the optical zone is important since it can capture the stresses and the variations of the displacements, and thus, the curvatures. The mesh refinement parameter is chosen by the operator as one of the variables to study for the regions of primary interest, such as the optical zone (i.e., the portion of the cornea central to the radial incisions), while the other regions such as the sclera are still incorporated in the model.

Figure 3:
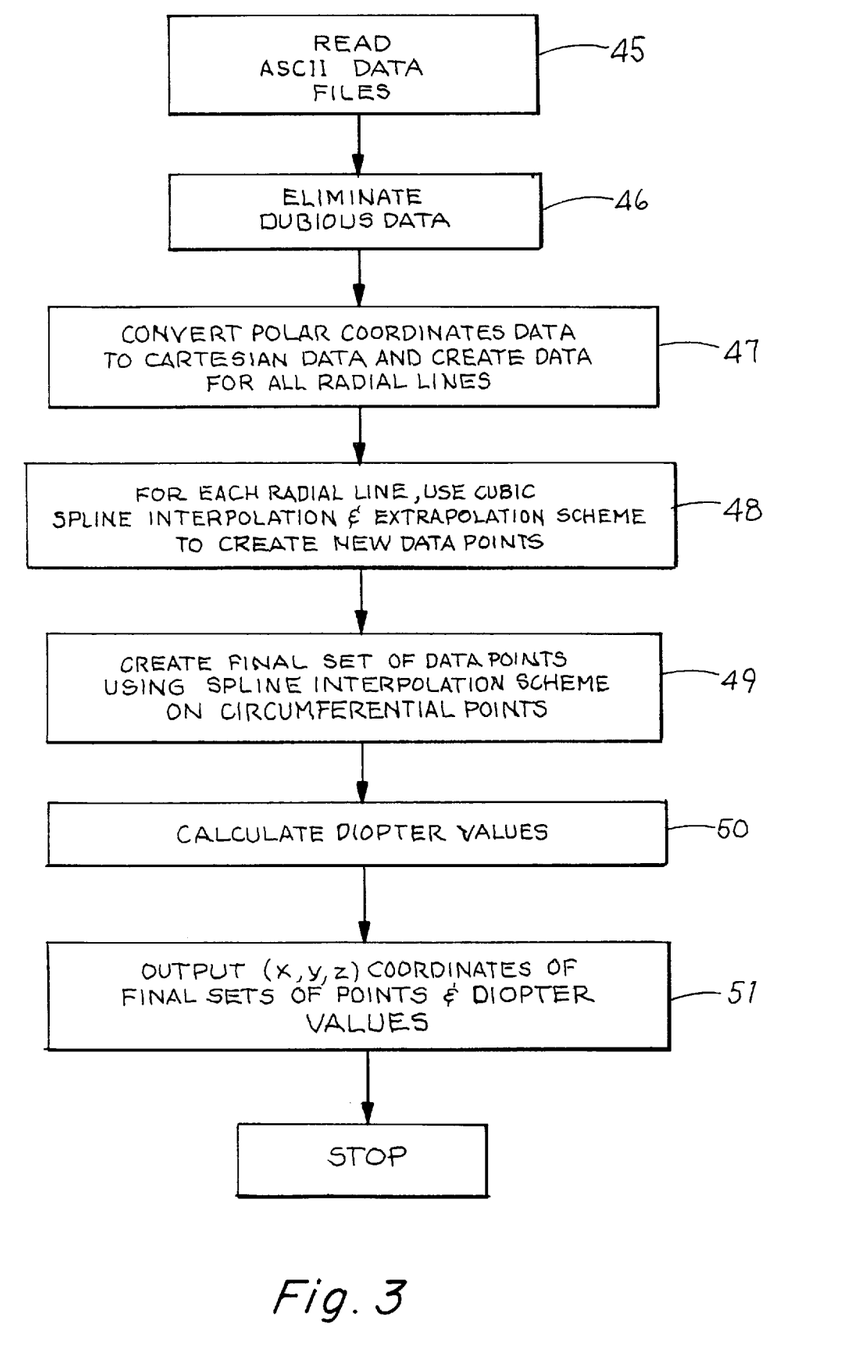
FIG. 3 is a block diagram of a subroutine executed in the course of executing block 35 of FIG. 2 to interpolate and extrapolate data in order to obtain the nodal coordinates of a finite element analysis model.
Figure 4:
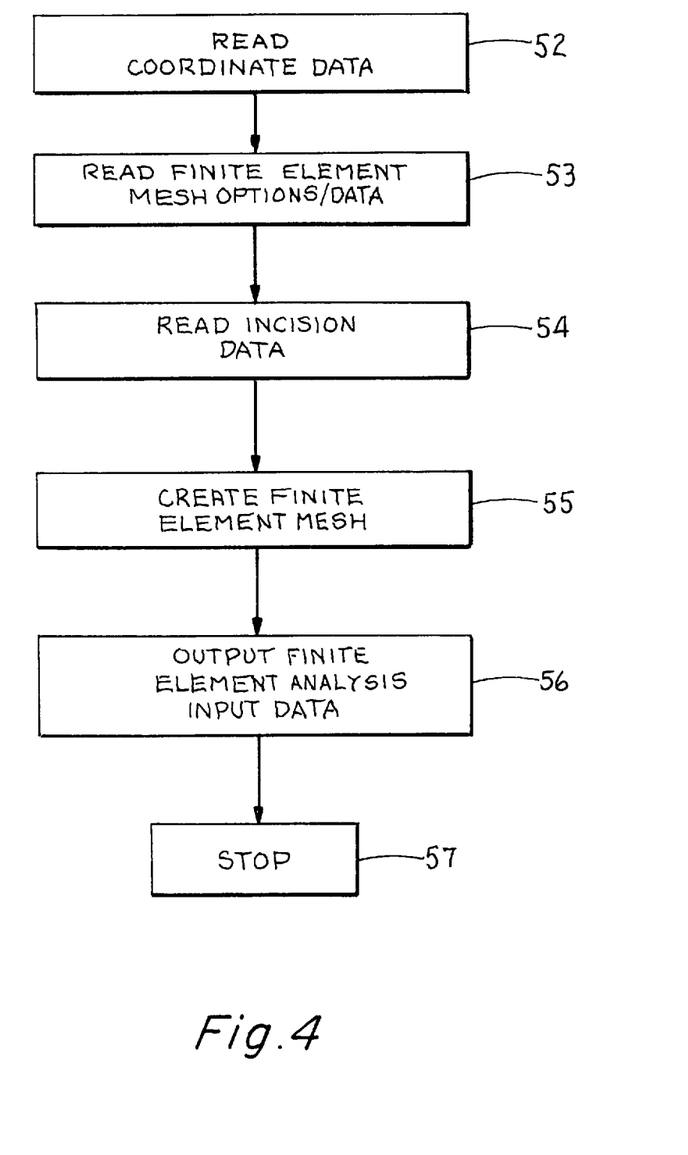
FIG. 4 is a block diagram of another subroutine executed in the course of executing block 35 or FIG. 2 to "construct" the finite element analysis model.

Some of the steps performed by computer 14 in accordance with block 35 of FIG. 2 are shown more specifically in FIGS. 3 and 4. As indicated in block 45 of FIG. 3, computer 14A reads the ASCII data files containing the above-mentioned 7000 coordinates of the corneal map produced by the TMS-1 corneal topographer 12. Due to the nature of the data collection, it is possible that some "noise" exists in the original data. The origin of the noise might be attributed to the inability of corneal topographer 12 to provide an exact determination of the coordinates, or the lack of existence of the coordinate value at an expected site. As indicated in block 46, a simple program scans the original data for elimination of such data points.

As indicated in block 47 of FIG. 3, the polar coordinate data supplied by the TMS-1 corneal topographer is converted into the above-mentioned 7000 x,y,z coordinates. Points which lie along the radial lines 21 of the FEA mesh shown in FIG. 5 are selected for use in the interpolation/extrapolation process described below.

As indicated in block 48, the cubic spline interpolation and extrapolation procedure (described later with reference to the diagram of FIG. 8) is utilized to compute the intermediate x,y,z coordinates for each node of the FEA mesh lying on the pre-defined radial line 21 (FIG. 5). Then, as indicated in block 49 of FIG. 3, the program creates a final set of x,y,z coordinates for nodes that lie on the circumferential lines 22 of the FEA mesh (FIG. 5) using the cubic spline interpolation/extrapolation method. This step is necessary since data points that have the same radial coordinate do not necessarily have the same height or z value.

At this stage, as indicated in block 50 of FIG. 3, the initial or pre-surgery diopter values at the final setup points are computed. Once the radial lines 21 are "generated", a series of nodes are selected at a specific height and used to obtain the circumferential nodes, i.e., the nodes which are on circumferential lines 22 "between" the radial lines 21. The x,y,z coordinates and diopter values of curvature at each node of the model then are output.

As indicated in block 52 the coordinate data files produced by block 51 of FIG. 3 are read. In block 53 the finite element mesh options/data are read. This includes the orthotropic material properties of the cornea and sclera, the nonlinear load-elongation curve data used by the "spring" elements which represent incision depth as subsequently described with reference to FIGS. 7 and 7A, the loading information (i.e., the intraocular pressure), and the boundary conditions (i.e., the connections of the bottom nodes of the sclera to a stationary reference). Then, the program reads the incision data, as indicated in block 54, and goes to block 55 in which the FEA model is "created", i.e., duplicate nodes, element connectivity and load-elongation data for the spring elements are created.

Finally, in block 56, the data files required for carrying out a geometric and materially nonlinear finite element analysis are created and output. In the present embodiment of the invention, the above-mentioned ABAQUS program is used as the finite element analysis program and is executed on the workstation computer 14B.

Returning to FIG. 2, in block 36, pre-operative curvatures are completed in diopters at each node of the FEA model.

Figures 7, 7A, 8:
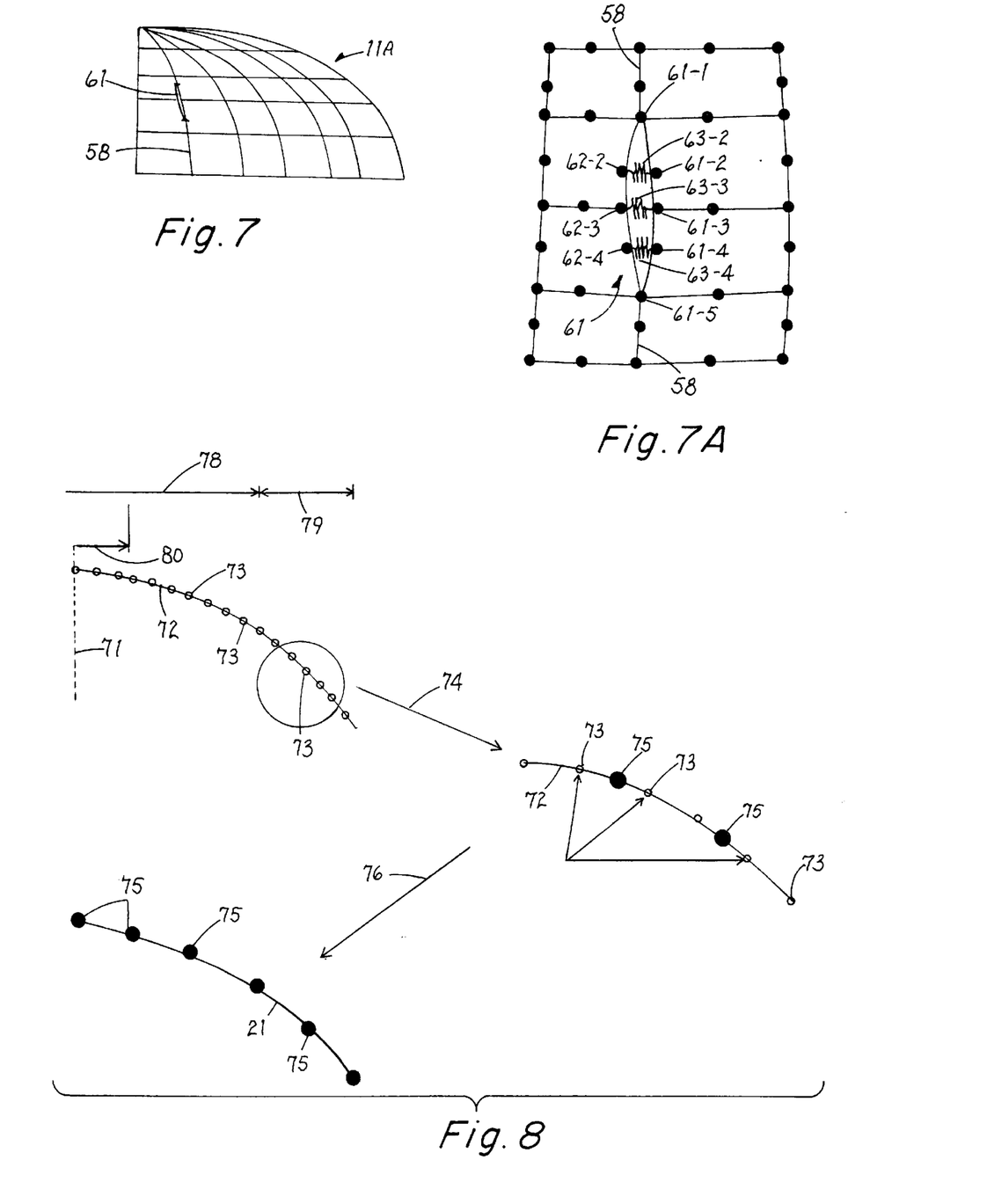
FIG. 7 is a diagram useful in explaining how incisions are included in the finite element analysis model of the present invention.
FIG. 7A is a diagram useful in conjunction with FIG. 7 in explaining modeling of incisions.
FIG. 8 is a diagram useful in explaining a technique for cubic spline interpolation and extrapolation to create "smoothed" three-dimensional data points from raw data provided by a keratoscope.

Then, in block 37, an initial (estimated) number of incisions are "constructed" in the FEA model using the information established in block 32. FIGS. 7 and 7A illustrate how each such incision is modeled in accordance with the present invention. In FIG. 7, the FEA mesh 11A includes an incision 61 modeled along a radial line 58 of the FEA mesh, in which numerals 61-1,2,3,4,5 represent all nodes of the FEA mesh from one end of the modeled incision 61 to the other. Additional "duplicate" nodes 62-2,3,4 are added to the FEA model, immediately adjacent to nodes 61-2,3,4, respectively. It should be noted that the "connectivity" of the nodes of the FEA mesh are omitted between corresponding duplicate nodes 62-1,2,3,4 and nodes 61-1,2,3,4, respectively.

These duplicate nodes are connected with spring elements 63-2,3,4 which have nonlinear load-deflection curves. The nature of the curves is a function of the depth of the incision and the material properties of the tissue through which the incision is made. The depth of the modeled incision 61 is represented by equations corresponding to the nonlinear elastic spring elements such as 63-1,2,3,4 in FIG. 7A, which are the only direct interconnections between the FEA mesh nodes and the immediately adjacent duplicate nodes. When an FEA program is executed, the effect of the intraocular pressure is to cause the incision 61 to "open" or spread an amount determined by the elastic spring constants assigned to the spring elements 63-1,2,3 and 4.

The above-mentioned ABAQUS FEA program, when executed as indicated in block 37 of FIG. 2, computes the displacements at each node of the FEA model in response to the intraocular pressure.

The computed nodal x,y,z displacements are added to the corresponding pre-operative x,y,z values for each node, and the results are stored in a data file. If desired, the results can be displayed in, for example, the form illustrated in FIG. 6. Post-operative curvatures (computed in diopters) then are computed for each node based on the new nodal locations.

Figure 6:
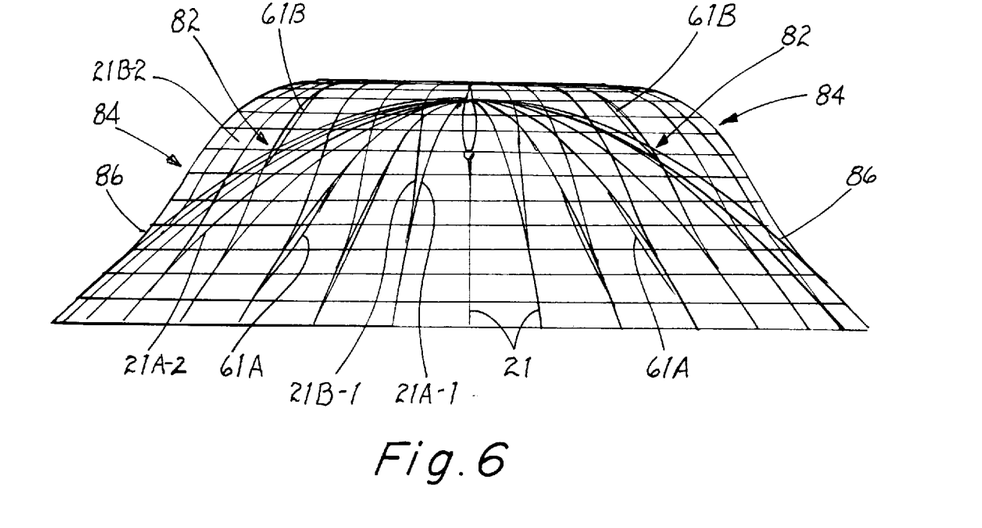
FIG. 6 is a partial side view illustrating both initial topography values of a portion of the cornea and final topography values resulting from simulated radial incisions and computed in accordance with the present invention.

In FIG. 6, which shows a computer printout produced by the system of FIG. 1, the measured pre-operative configuration of the eye surface is indicated by radial lines 82, and the computed post-operative configuration is indicated by radial lines 84. Numerals 21 generally indicate radial lines of the FEA model, as in FIG. 5. More specifically, numerals 21A-1 and 21A-2 designate radial lines of the pre-operative surface represented in the FEA model, and numerals 21B-1 and 21B-2 represent radial lines of the "computed" post-operative surface in the FEA model. Numerals 61A designate proposed radial incisions in the "measured" pre-operative surface, and numerals 61B designate the same incisions in the "computed" post-operative surface. (The individual circumferential lines of the computer printout of FIG. 6 are difficult to identify, but this does not prevent accurate interpretation of the effect of the proposed incisions on the curvature of the cornea.) Numerals 86 indicate the limbus.

As indicated in block 38, the post-operative curvatures then are compared with the pre-operative curvatures and the vision objectives established according to block 31 to determine whether the initial estimated surgical plan accomplished the vision objectives.

Figure 10:
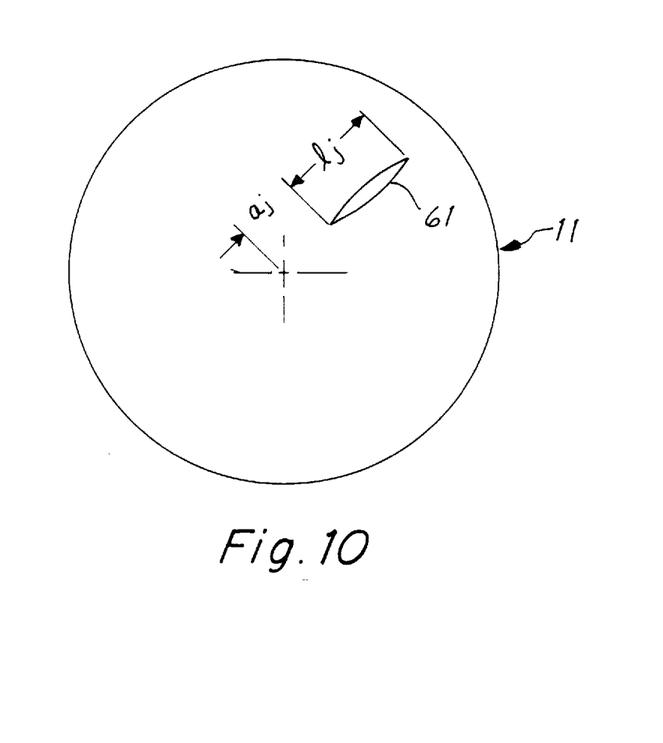
FIG. 10 is a diagram useful in explaining optimization of the surgical plan according to block 41 of FIG. 2.

Then, as indicated in block 39, computer 14 determines if the vision objectives are met. If the determination of decision block 39 is affirmative, the surgical design is complete, as indicated in label 40. Otherwise, however, the program executed by computer 14 goes to block 41, and an optimization technique, subsequently described with reference to FIG. 10, is utilized to modify the number of incisions and their locations, orientations, lengths, and depths. The process then returns to block 37 and repeats until an affirmative determination is reached in decision block 39.

The technique for modifying and optimizing the surgical design according to block 41 can be understood with reference to FIG. 10. As indicated above, the vision objectives are to obtain prescribed curvature values at specific FEA nodal locations i on the cornea. As an example, assume the surgical plan includes the locations of the incisions and includes the location and depth of each incision. The surgical optimization problem of block 41 then can be defined to be the problem of determining a value of $\{a_j,l_j,d_j\}$ that minimizes the value of the expression $$f(a_j, l_j, d_j) = \sum_{i=1}^{n} \left( \frac{r_i}{\hat{r}_i} - 1 \right)^2 \tag{11}$$

with $$a_j^L \leq a_j \leq A_j^U$$
$$l_j^L \leq l_j \leq l_j^U$$
$$d_j^L \leq d_j \leq d_j^U$$

where $\{a_j,l_j,d_j\}$ is the vector of design variables, $f\{a_j,l_j,d_j\}$ is the objective function, $a_j$ is the starting radial distance from the center of the finite element model, as shown in FIG. 10, $l_j$ is the length of the incision, $d_j$ is the depth of the incision, j is the incision number, $r_i$ is the computed curvature value based on the results from the finite element analysis, $\hat{r}_i$ is the observed curvature, n is the number of points at which curvature computations are to be carried out, and the three above inequality constraints represent the lower (L) and upper (U) bounds on the three design parameters.

With this information, it is possible to include any parameter that influences the finite element model as a potential design variable, and any response or parameters related to the response computed by the finite element analysis as appearing in the objective functions or constraints. For example, the shape of the incision, the number of incisions, or the thickness of ablative tissue can be design variables.

The foregoing problem formulation falls under the category of nonlinear programming problem. Those skilled in the art can readily solve such problems using nonlinear programming techniques utilizing commercially available nonlinear programming software, such as the previously mentioned DOT program.

It should be understood that computer 14 includes not only IBM PC-type computer 14A (which can be a 86386 or 86486 based computer), but also a workstation computer 14B, merely because the ABAQUS program cannot be executed on a PC-type computer. If, in the future, a suitable FEA analysis program becomes available, all of the computation can be performed by an IBM PC-type computer 14A.

FIG. 8 is useful in illustrating the application of cubic spline techniques referred to in block 48 of FIG. 2 to interpolate/extrapolate data from the nodal points of the FEA mesh from the data points obtained from TMS-1 corneal topographer 12. In FIG. 8, numeral 71 designates the z axis or a center line of the cornea passing through its apex, numeral 72 designates a radial line along which data points obtained from corneal topographer 12 lie, and numeral 73 designates various such measured data points. The extent of the cornea is indicated by arrow 78, and the extent of the sclera is indicated by arrow 79. The extent of the "optical zone" is indicated by arrow 80. As indicated above, the TMS-1 corneal topographer provides 7000 such data points 73. The first step of the cubic spline process takes such data points, as indicated by arrow 74, and "fits" each segment of radial line 72 between adjacent corneal topographer data points 73 to the equation $$z=ax^3+bx^2+cx+d, \tag{12}$$

where z is a distance along center line 71, and x is distance in the horizontal direction from line 71 toward the base of the sclera. Equation 12 then is used to compute values of z for each value of x corresponding to a node of the FEA mesh (shown in FIG. 5) to obtain values z for each of the nodes of the FEA mesh along each radial line 21, as indicated by arrow 76 in FIG. 8. Values for the "midpoint" nodes such as 26-2 and 26-6 of FIG. 5 are obtained by interpolating adjacent nodal values of z on the same circumferential line 22. Most texts on numerical analysis disclose details on how to use the cubic spline technique, and various commercially available programs, such as IMSL, available from IMSL, Inc. of Houston, Tex., can be used.

A fixed boundary condition for the base of the sclera can be assigned. It has been found that the nature of the boundary conditions at the base of the sclera has only a small effect on the results of the finite element analysis of the cornea.

The above-described model was utilized to compute the strains and nodal deflections in a particular patient's eye based on measured topographical data extending outward approximately 8 millimeters from the center of a patient's eye. The measured data was extrapolated outward another 8 millimeters to approximate the topography of the remaining cornea. Computed results for six eyes of four different patients using the above FEA model agreed with clinically measured results to within one to ten percent. It is expected that when the back-calculation of Young's modulus is incorporated into the process, agreement will be improved, especially in the optical zone and close to incisions.

The above-described FEA model can be used to pre-operatively design incisions, excisions or ablations of the cornea, resulting in great predictability of surgical outcome and thereby allowing minimum invasiveness to achieve the desired result with the least amount of surgical trauma to the cornea. Fewer operative and post-operative visits by the patient to the surgery clinic are likely. Advantages of the improved surgical designs which result from the above-described invention include reduced multi-focal imaging of the central cornea, thereby enhancing contrast sensitivity and improving vision under low light illumination conditions. Reduction or elimination of post-operative irregular astigmatism is another benefit. Yet another benefit is minimization of side effects such as glare and fluctuation of vision associated with traditional incisional keratotomy. The described mathematical model will have other uses, such as allowing design of a bifocal corneal curvature to allow both near and distance vision for patients in the presbyopic stage of their lives. The model of the present invention also will allow development of new surgical techniques for correcting nearsightedness, farsightedness and astigmatism as a viable alternative to experimenting on live human corneas.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

For example, keratoscopes or other cornea measurement devices than the TMS-1 device can be used. Non-radial incisions, such as T-shaped incisions for correcting astigmatism, can be readily modeled. The stresses at various locations can be displayed, for example, by graded colors. Many variations of the finite element model are possible. In the two-dimensional shell finite element analysis model described above, the use of the nonlinear springs to model depths of incisions could be avoided by modeling elements around the proposed incision to have reduced thickness and/or different material properties, so that the incision region has reduced stiffness, and the computed deformations are essentially the same as if the nonlinear springs were to be used. For example, it is possible to use three-dimensional finite elements in lieu of the two-dimensional shell finite elements with assigned thickness parameters, and model the incisions directly, without having to use the nonlinear spring elements. Mathematical models other than a finite element analysis model can be used. For example, a boundary element analysis model could be used. As those skilled in the art know, the basic steps in the boundary element methods are very similar to those in the finite element methods. However, there are some basic differences. First, only the boundary is discretized, that is, the elements are "created" only on the boundary of the model, whereas in finite element analysis models the elements are "created" throughout the domain of the model. Second, the fundamental solution is used which satisfies the governing differential equation exactly. A fundamental solution is a function that satisfies the differential equation with zero right hand side (i.e., with body force set to zero) at every point of an infinite domain except at one point known as the source or load point at which the right hand side of the equation is infinite. Third, the solution in the interior of the model can be obtained selectively once the approximate solution on the boundary is computed. Although constant intraocular pressure has been assumed, non-constant intraocular pressure could be incorporated into the described technique. Although post-operative swelling has been assumed to not effect the eventual curvatures of the cornea, healing of the incision does effect the eventual curvature. The finite element analysis model can be adapted to model such healing effects and predict the final curvatures, stresses, etc.

Additionally, p-finite elements, Raleigh-Ritz, mixed formulations, Reissner's Principal, all can be used to generate the finite element equations. These equations, then, can be used in the modeling method of the present invention.

What is claimed is:

1. A computer-implemented method of simulating patient specific corneal deformation in response to a corneal incision, comprising the steps of:

(a) measuring the topography of a portion of the patient's eye using a topography measuring device to produce patient specific x,y,z coordinates for a number of patient specific data points of the surface of the patient's eye;

(b) storing in a storage means a mathematical analysis model of the patient's eye, the model including a number of nodes, the connectivities of which define a plurality of elements;

(c) determining a value representing intraocular pressure in the patient's eye and assigning that value to each element;

(d) representing an incision in the mathematical analysis model by assigning at least one of a thickness and a value of the modulus of elasticity to elements surrounding the incision computed from the value determined in step (c); and (e) using the mathematical analysis model to compute new values of the patient specific x,y,z coordinates resulting from the incision at each of the nodes, respectively.

2. A computer-implemented method of simulating patient specific corneal deformation in response to corneal incisions, comprising the steps of:

(a) measuring the topography of a portion of the patient's eye using a topography measuring device to produce patient specific x,y,z coordinates for a large number of patient specific data points of the surface of the patient's eye;

(b) storing in a storage means operably associated with a computer system for implementing the computer-implemented method, a mathematical analysis model of the patient's eye, the model including a number of nodes, the connectivities of which define a plurality of elements;

(c) determining a value representing intraocular pressure in the patient's eye and assigning that value to each element;

(d) representing the incision in the mathematical analysis model by means of a plurality of duplicate nodes adjacent to a group of incision-bounding nodes of the mathematical analysis model located along the incision and representing the depth of the incision by means of a plurality of nonlinear spring elements each connecting an incision-bounding node to an adjacent duplicate node, respectively each of the plurality of nonlinear spring elements having a load deflection curve based upon depth of incision and the value obtained from step (c); and (e) using the mathematical analysis model to compute new values of the patient specific x,y,z coordinates resulting from the incision at each of the nodes, respectively.

3. The computer-implemented method of claim 2 including establishing at least one vision objective for the patient's eye, wherein step (e) includes comparing the simulated deformation of the cornea with the vision objective to determine if the incision results in the vision objective being met, and, if the vision objective is not met, modifying the incision and/or adding another incision in the mathematical analysis model and repeating step (e) to determine if the at least one vision objective is met.

4. A computer-implemented method of simulating patient specific corneal deformation as a result of a corneal ablation, comprising the steps of;

(a) measuring the topography of a portion of the patient's eye using a topography measuring device to produce patient specific x,y,z coordinates for a number of patient specific data points of the surface of the patient's eye;

(b) storing in a storage means a mathematical analysis model of the patient's eye, the model including a predetermined number of nodes, the connectivities of which define a plurality of elements;

(c) determining at least one material properties value, by the use of at least one of topography, ultrasound, pachymetry or global measurements, representing the material properties of the cornea and assigning at least one the material properties value to each element;

(d) representing the ablation of the cornea in the mathematical analysis model by assigning at least one of reduced values of the thickness and a reduced value of the modulus of elasticity to elements corresponding to the ablated portion of the cornea; and (e) using the mathematical analysis model to compute new values of the patient specific x,y,z coordinates resulting from the ablation at each of the nodes, respectively.

5. The computer-implemented method of claim 4 including establishing at least one vision objective for the patient's eye, wherein step (e) includes comparing the simulated deformation of the cornea with the vision objective to determine if the ablation results in the vision objective being met, and, if the vision objective is not met, modifying the ablation in the mathematical analysis model and repeating step (e) to determine if the at least one vision objective is met.

6. A computer-implemented method of simulating patient specific corneal deformation in response to a corneal incision, comprising the steps of:

(a) measuring the topography of at least a portion of the patient's eye using a topography measuring device to produce patient specific x,y,z coordinates for each of a plurality of patient specific data points of a surface of the patient's eye;

(b) storing in a storage means associated with the computer system a finite element analysis model of the patient's eye, the finite element analysis model including a number of nodes, the connectivities of which define a plurality of elements;

(c) operating a processing means which interfaces with the storage means to interpolate between and extrapolate beyond the patient specific data points to obtain a reduced number of patient specific x,y,z coordinates that correspond to nodes of the finite element analysis model, respectively, and assigning the reduced number of patient specific x,y,z coordinates to the various nodes, respectively;

(d) determining at least one material properties value of the patient's eye, by the use of at least one of topography, ultrasound, pachymetry or physical dimensions of the eye and assigning the at least one material properties value to each finite element;

(e) representing a first incision in the finite element analysis model by means of a plurality of duplicate nodes adjacent to a group of incision-bounding nodes of the finite element analysis model located along the first incision and representing the depth of the first incision by means of a plurality of nonlinear spring elements having load deflection curves based upon the at least one material property value determined in step (d) and incision depth, each nonlinear spring element connecting an incision-bounding node to an adjacent duplicate node, respectively, by shell modeling;

(f) using the finite element analysis model to compute at each of the nodes, new values of the patient specific x,y,z coordinates resulting from the first incision; and (g) displaying the nodes having the computed patient specific x,y,z coordinates to show the simulated deformation of the cornea.

7. The computer-implemented method of claim 1 including establishing at least one vision objective for the patient's eye, said at least one vision objective being selected from the group consisting of visual acuity, duration of treatment, absence of side effects, low light vision, astigmatism, contrast and depth perception, and storing vision objective information in the storage means, wherein step (f) includes comparing the simulated deformation of the cornea with the vision objective information to determine if the first incision results in the vision objective being met.

8. The computer-implemented method of claim 7 including, if the vision objective is not met, modifying the first incision and/or adding a second incision in the finite element analysis model similar to the first incision, and repeating step (f) to determine if the vision objective is met.

9. The method of claim 8 wherein step (c) includes executing the finite element analysis model so as to minimize the total potential energy of the surface of the patient's eye represented in the finite element analysis model.

10. The computer-implemented method of claim 9 including measuring the thickness of various points of the cornea and/or sclera and assigning values of the measured thicknesses to each element of the finite element analysis model, respectively, before step (f).

11. The computer-implemented method of claim 9 including modeling an ablation of the cornea in the finite element analysis model by assigning a plurality of values of thickness corresponding to an ablated portion of the cornea to elements of the finite element analysis model in the ablated portion of the cornea, respectively.

12. The computer-implemented method of claim 9 wherein step (e) includes representing a plurality of radial keratotomy incisions, including the first and second incisions, in the finite element analysis model.

13. The computer-implemented method of claim 9 wherein the first incision is a non-radial incision.

14. The computer-implemented method of claim 9 including assigning values of material constants of the eye, including Poisson's ratio, modulus of elasticity, and shear modulus, to each element of the finite element analysis model.

15. The computer-implemented method of claim 12 wherein the modifying includes executing a nonlinear programming computer program to determine how much to modify the number of incisions, the orientations of the incisions, and the lengths and depths of the various incisions.

16. The computer-implemented method of claim 7 wherein establishing the at least one vision objective includes providing an initial set of surface curvatures for the cornea, the computer-implemented method including computing simulated post-operative curvatures from the new values of patient specific x,y,z coordinates computed in step (f) and comparing the simulated post-operative curvatures with the surface curvatures of the initial set to determine if the at least one vision objective is met.

17. The method of claim 7 wherein each element of the finite element analysis model is an eight-node element, and wherein a boundary condition of the finite element analysis model is that a base portion of the finite element analysis model is stationary.

18. The method of claim 8 including assigning substantially different measured values of modulus of elasticity to elements of cornea portions and sclera portions of the finite element analysis model.

19. The computer-implemented method of claim 1 wherein step (c) includes executing a cubic spline computer program to obtain the reduced number of patient specific x,y,z coordinates according to an equation $z=ax^3+bx^2+cx+d$ which has been fit to the measured patient specific data points of step (a), x being a distance from an apex axis of the patient's eye.

20. The computer-implemented method of claim 8 including selecting at least one vision objective for each patient which produces a simulated multi-focal configuration of the cornea.

21. A computer-implemented method of simulating patient specific corneal deformation as a result of a corneal ablation on a patient's eye, comprising the steps of:
   (a) measuring the topography of a portion of the patient's eye using a topography measuring device to produce patient specific x,y,z coordinates for a number of patient specific data points of a surface of the patient's eye;
   (b) storing in a storage means associated with a computer system used for the computer-implemented method, a finite element analysis model of the patient's eye, the finite element analysis model including a predetermined number of nodes, the connectivities of which define a plurality of elements,
   (c) operating processing means operatively associated with the computer system to interpolate between and extrapolate beyond the patient specific data points to obtain a reduced number of patient specific x,y,z coordinates that correspond to nodes of the finite element analysis model, respectively, and assigning the x,y,z coordinates to the various nodes, respectively;
   (d) determining at least one material property of the cornea and assigning the at least one material property value to each finite element;
   (e) representing an ablation of the cornea in the finite element analysis model by assigning values of thicknesses, derived from the at least one material property from step (d) corresponding to the ablated portion of the cornea to nodes of the finite element analysis model in the ablated portion, respectively;
   (f) using the finite element analysis model, computing new values of the patient specific x,y,z coordinates at each of the nodes to simulate deformation of the cornea resulting from the proposed ablation; and
   (g) operating the processing means to display the computed patient specific x,y,z coordinates to show the simulated deformation of the cornea.

22. A computer-implemented method of determining the modulus of elasticity of patient specific tissue at a plurality of locations of the surface thereof, comprising the steps of:
   (a) storing in a storage means operatively associated with a compute system used for the computer-implemented method, a finite element analysis model of the patient specific tissue, the finite element analysis model including a number of nodes, the connectivities of which define a plurality of elements;
   (b) applying a known external pressure to the patient specific tissue and then measuring the topography of a at least a portion of the patient specific tissue under the influence of the applied external pressure using a topography measuring device to produce patient specific x,y,z coordinates for a number of patient specific data points of the surface of the patient specific tissue and then remapping the topography by backcalculating the data;
   (c) operating processing means operatively associated with the computer system to interpolate between and extrapolate beyond the patient specific data points to obtain a reduced number of patient specific x,y,z coordinates that correspond to nodes of the finite element analysis model, respectively, and assigning the reduced number of patient specific x,y,z coordinates to the various nodes, respectively, and assigning the value of the external pressure to elements of the finite element analysis model corresponding to locations of the patient specific tissue to which the known external pressure is applied in step (b);
   (d) determining a value representing intra-tissue pressure in the patient specific tissue and assigning that value to each element;
   (e) assigning initial values of the modulus of elasticity to each element, respectively, of the finite element analysis model;
   (f) using the finite element analysis model, computing new values of the patient specific x,y,z coordinates at each of the nodes to simulate deformation of the patient specific tissue resulting from the external pressure and the intra-tissue pressure for the initial values of the modulus of elasticity;
   (g) operating the processing means to compare the new values of the patient specific x,y,z coordinates computed in step (f) with the patient specific x,y,z coordinates recited in step (c);
   (h) operating the processing means to modify values of the modulus of elasticity of the various elements of the finite element analysis model, respectively, if the comparing of step (g) indicates that a difference between the patient specific x,y,z coordinates of step (c) and the patient specific x,y,z coordinates computed in step (f) exceeds a predetermined criteria; and
   (i) repeating steps (f) through (h) until final values of the modulus of elasticity at each finite element are obtained.

23. A computer-implemented method of determining change of a cornea of a patient's eye as a result of an ablation on the cornea, the computer-implemented method including the steps of:

(a) storing in a storage means operatively associated with a computer system for implementing the computer-implemented method, a finite element analysis model of a patient's eye, the finite element analysis model including a number of nodes, the connectivities of which define a plurality of elements;

(b) applying a known external pressure to the patient's eye and then measuring the topography of a portion of the patient's eye using a topography measuring device to produce patient specific x,y,z coordinates for a number of patient specific data points of the pressure-deformed surface of the patient's eye and then remapping the topography by backcalculating the data;

(c) operating a processing means operatively associated with the computer system to interpolate between and extrapolate beyond the patient specific data points to obtain a reduced number of patient specific x,y,z coordinates that correspond to the nodes of the finite element analysis model, respectively, and assigning the reduced number of patient specific x,y,z coordinates to the various nodes respectively, and assigning the value of the external pressure to elements of the finite element analysis model corresponding to locations of the patient's eye to which the external pressure is applied in step (b);

(d) determining a value representing intraocular pressure in the patient's eye and assigning that value to each element;

(e) assigning initial values of the modulus of elasticity to each element, respectively, of the finite element analysis model;

(f) using the finite element analysis model, computing new values of the patient specific x,y,z coordinates at each of the nodes to simulate deformation of the cornea resulting from the external pressure and the intraocular pressure for the initial values of the modulus of elasticity;

(g) comparing the new values of the patient specific x,y,z coordinates computed in step (f) with the patient specific x,y,z coordinates recited in step (c);

(h) operating the processing means to modify values of the modulus of elasticity of the elements of the finite element analysis model, respectively, if the comparing of step (g) indicates a difference between the patient specific x,y,z coordinates obtained in step (c) and the patient specific x,y,z coordinates computed in step (f) exceeds a predetermined criteria;

(i) repeating steps (f) through (h) until final values of the modulus of elasticity are obtained;

(j) representing ablation of at least one portion of the patient's cornea in the finite element analysis model by assigning values of thicknesses corresponding to the ablated portion of the cornea to elements of the finite element analysis model in the ablated portion of the cornea, respectively;

(k) using the finite element analysis model, computing new values of the patient specific x,y,z coordinates at each of the nodes to simulate deformation of the cornea resulting from the proposed ablation;

(l) comparing the simulated deformation of the cornea with at least one pre-established vision objective for the patient's eye, said at least one pre-established vision objective being selected from the group consisting of visual acuity, duration of treatment, absence of side effects, low light vision, astigmatism, contrast and depth perception, to determine if the ablation results in the vision objective being met; and (m) if the vision objective is not met, modifying the proposed ablation in the finite element analysis model and repeating steps (j) through (l) until the at least one pre-determined vision objective is met.

24. A computer-implemented method of simulating change of a cornea of patient specific patient's eye as a result of a proposed incision on the cornea, the computer-implemented method including the steps of;

(a) storing in a storage means operatively associated with a computer system used for the computer-implemented method, a finite element analysis model of a patient's eye, the finite element analysis model including a number of nodes, the connectivities of which define a plurality of elements;

(b) applying a known external pressure to the patient's eye and then measuring the topography of a portion of the patient's eye under the influence of the externally applied pressure using a topography measuring device to produce patient specific x,y,z coordinates for a number of patient specific data points of the surface of the patient's eye and then remapping the topography by backcalculating the data;

(c) operating a processing means associated with the computer system to interpolate between and extrapolate beyond the patient specific data points to obtain a reduced number of patient specific x,y,z coordinates that correspond to the nodes of the finite element analysis model, respectively, and assigning the reduced number of patient specific x,y,z coordinates to the various nodes respectively, and assigning the value of the external pressure to elements of the finite element analysis model corresponding to locations of the patient's eye to which the external pressure is applied in step (b);

(d) determining a value representing intraocular pressure in the patient's eye and assigning that value to each element;

(e) assigning initial values of the modulus of elasticity to each element, respectively, of the finite element analysis model;

(f) using the finite element analysis model, computing new values of the patient specific x,y,z coordinates at each of the nodes to simulate deformation of the cornea resulting from the external pressure and the intraocular pressure for the initial values of the modulus of elasticity;

(g) comparing the new values of the patient specific x,y,z coordinates computed in step (f) with the patient specific x,y,z coordinates recited in step (c);

(h) operating the processing means to modify values of the modulus of elasticity of the elements of the finite element analysis model respectively, if the comparing of step (g) indicates a difference between the patient specific x,y,z coordinates obtained in step (c) and the patient specific x,y,z coordinates computed in step (f) exceeds a predetermined criteria;

(i) repeating steps (f) through (h) until a final value of the modulus of elasticity is obtained;

(j) representing the incision in the finite element analysis model, by shell modeling, by means of a plurality of duplicate nodes adjacent to a group of incision-bounding nodes of the finite element analysis model located along the incision and representing the depth of the incision by means of a plurality of nonlinear spring elements, the plurality of nonlinear spring elements having load deflection curves which are a function of the final value of the modulus of elasticity obtained from step (i) and incision depth, each of the plurality of nonlinear spring elements connecting an incision-bounding node to an adjacent duplicate node, respectively;

(k) using the finite element analysis model, computing new values of the patient specific x,y,z coordinates at each of the nodes to simulate deformation of the cornea resulting from the incision and the intraocular pressure;

(l) comparing the simulated deformation of the cornea with at least one pre-established vision objective for the patient's eye to determine if the incision results in the at least one vision objective being met; and (m) if the vision objective is not met, modifying the incision in the finite element analysis model and repeating steps (j) through (l) until the vision objective is met.

25. A system for computer-implemented simulation of patient specific corneal deformation in response to a corneal incision, comprising in combination:

(a) a computer processing means for receiving instructions from a computer program and processing said instructions with input data, said instructions and input data including a finite element analysis model of a patient's eye, the finite element analysis model including a predetermined number of nodes, the connectivities of which define a plurality of elements;

(b) corneal topographer means for measuring the topography of at least a portion of the patient's eye to produce patient specific x,y,z coordinates for a number of patient specific data points of the surface of the patient's eye;

(c) means in the computer processing means for interpolating between and extrapolating beyond the patient specific data points to obtain a reduced number of patient specific x,y,z coordinates that correspond to nodes of the finite element analysis model, respectively, and assigning the reduced number of patient specific x,y,z coordinates to the various nodes, respectively;

(d) means for measuring a material properties value, by the use of at least one of topography, ultrasound, pachymetry or global measurements, representing the material properties of the cornea;

(e) means for inputting the material properties value into the finite element analysis model and assigning the material properties value to each element;

(f) shell modeling means resident in the computer processing means for representing a first incision in the finite element analysis model by means of a plurality of duplicate nodes adjacent to a group of incision-bounding nodes of the finite element analysis model located along the first incision and representing a depth of the first incision by means of a plurality of nonlinear spring elements each connecting an incision-bounding node to an adjacent duplicate node, respectively;

(g) means in the computer processing means for executing a program including the finite element analysis model to compute new values of the patient specific x,y,z coordinates resulting from the first incision at each of the nodes, respectively; and (h) means responsive to the computer processing means for displaying the nodes having the computed patient specific x,y,z coordinates to show the deformation of the cornea.

26. The system of claim 25 including means in the computer processing means for comparing the simulated deformation of the cornea with at least one pre-established vision objective for the patient's eye to determine if the first incision results in the at least one vision objective being met, and means for modifying the first incision and/or adding a second incision in the finite element analysis model similar to the first incision if the vision objective is not met.

27. The system of claim 26 including means for measuring the thickness of various points of the cornea and/or sclera, and means for inputting the thicknesses into the computer processing means and assigning values of the measured thicknesses to each element of the finite element analysis model, respectively.

28. The system of claim 27 wherein the modifying means includes a nonlinear programming computer program to determine how much to modify the number of incisions, the orientations of the incision, and the lengths and depths of the various incisions.

29. A computer-implemented method of simulating change of a patient's cornea as a result of a proposed ablation on the cornea, the computer-implemented method using a computer system having and including the steps of:

(a) storing in a storage means operably associated with the computer system, a mathematical analysis model of a patient's eye, the finite element analysis model including a number of nodes, the connectivities of which define a plurality of elements;

(b) applying a known external pressure to the patient's eye and then measuring the topography of a portion of the patient's eye under the influence of the externally applied pressure using a topography measuring device to produce patient specific x,y,z coordinates for a number of patient specific data points of the surface of the patient's eye and then remapping the topography by backcalculating the data;

(c) operating processing means associated with the computer system to interpolate between and extrapolate beyond the patient specific data points to obtain a reduced number of patient specific x,y,z coordinates that correspond to the nodes of the finite element analysis model, respectively, and assigning the reduced number of patient specific x,y,z coordinates to the various nodes respectively, and assigning the value of the external pressure to elements of the finite element analysis model corresponding to locations of the patient's eye to which the external pressure is applied in step (b);

(d) determining a value, by the use of topography, ultrasound, pachymetry or global measurements, representing the material properties of the cornea and assigning that value to each element;

(e) assigning initial values of the modulus of elasticity to each element, respectively, of the finite element analysis model;

(f) using the mathematical analysis model, computing new values of the patient specific x,y,z coordinates at each of the nodes to simulate deformation of the cornea resulting from the external pressure and the intraocular pressure for the initial values of the modulus of elasticity;

(g) comparing the new values of the patient specific x,y,z coordinates computed in step (f) with the patient specific x,y,z coordinates recited in step (c);

(h) operating the processing means to modify values of the modulus of elasticity of the elements of the finite element analysis model, respectively, if the comparing of step (g) indicates a difference between the patient specific x,y,z coordinates obtained in step (c) and the patient specific x,y,z coordinates computed in step (f) exceeds a predetermined criteria;

(i) repeating steps (f) through (h) until a final value of the modulus of elasticity is obtained;

(j) representing a proposed ablation of the cornea in the mathematical analysis model by assigning at least one of value represent a changed value of thickness and a changed value of the modulus of elasticity to elements corresponding to the ablated portion of the cornea;

(k) using the finite element analysis model, computing new values of the patient specific x,y,z coordinates at each of the nodes to simulate deformation of the cornea resulting from the ablation and the intraocular pressure;

(l) comparing the simulated deformation of the cornea with a pre-established vision objective for the patient's eye to determine if the ablation results in the vision objective being met; and (m) if the vision objective is not met, modifying the ablation in the finite element analysis model and repeating steps (j) through (l) until the vision objective is met.

* * * * *